US012703671B2

(12) United States Patent
Reich et al.

(10) Patent No.: US 12,703,671 B2
(45) Date of Patent: Aug. 11, 2026

(54) PROCESS FOR TREATING A GAS STREAM FROM PLASTIC PYROLISIS AND/OR BIOMASS PYROLISIS, AND INSTALLATION FOR INTEGRATION INTO A STEAM CRACKER

(71) Applicant: TECHNIP ENERGIES FRANCE, Nanterre Cedex (FR)

(72) Inventors: Veronique Reich, Vaucresson (FR); Yvon Simon, Le Trait (FR); Walkiria Braga, Courbevoie (FR)

(73) Assignee: TECHNIP ENERGIES FRANCE, Nanterre Cedex (FR)

( * ) Notice: Subject to any disclaimer, the term of this patent is extended or adjusted under 35 U.S.C. 154(b) by 882 days.

(21) Appl. No.: 17/841,066

(22) Filed: Jun. 15, 2022

(65) Prior Publication Data

US 2022/0402840 A1 Dec. 22, 2022

(30) Foreign Application Priority Data

Jun. 16, 2021 (FR) ...................................... 2106391

(51) Int. Cl.

| | |
|---|---|
| ***C07C 7/11*** | (2006.01) |
| ***B01D 53/04*** | (2006.01) |
| ***B01D 53/14*** | (2006.01) |
| ***C07C 7/10*** | (2006.01) |
| ***F25J 3/02*** | (2006.01) |

(52) U.S. Cl.

CPC ................ *C07C 7/11* (2013.01); *B01D 53/04* (2013.01); *B01D 53/1456* (2013.01); *C07C 7/10* (2013.01);

(Continued)

(58) Field of Classification Search

CPC ................ B01D 53/1487; B01D 53/04; B01D 53/1456; B01D 53/1437; B01D 2253/104;

(Continued)

(56) References Cited

U.S. PATENT DOCUMENTS

| | | | | |
|---|---|---|---|---|
| 6,271,433 | B1 | 8/2001 | Keady et al. | |
| 6,441,263 | B1 * | 8/2002 | O'Rear | C07C 15/00 585/650 |

(Continued)

FOREIGN PATENT DOCUMENTS

| | | | |
|---|---|---|---|
| DE | 102010013658 | A1 | 10/2011 |
| FR | 2829401 | A1 | 3/2003 |

OTHER PUBLICATIONS

Achkan Bagheri et al., "Engineering for success", Hydrocarbon Engineering magazine, Aug. 2020. (Year: 2020).*

(Continued)

*Primary Examiner* — Prem C Singh
*Assistant Examiner* — Brandi M Doyle
(74) *Attorney, Agent, or Firm* — Troutman Pepper Locke LLP; Gabrielle L. Gelozin

(57) ABSTRACT

This process comprises quenching and washing with water a gas stream derived from pyrolysis, and separating an aqueous phase from a washed gas stream; compressing, then cooling a washed gas stream; washing the compressed gas stream under pressure; passing the washed gas stream through at least one acid removal unit; drying the acid-depleted gas stream; passing the dry gas stream through at least one impurity removal unit; and feeding the purified gas stream into a cryogenic absorption unit and supplying the cryogenic absorption unit with a hydrocarbon cryogenic solvent to obtain a light gas residue, and a fraction of $C_2^+$ hydrocarbons.

19 Claims, 2 Drawing Sheets

(52) U.S. Cl.
CPC ....... *F25J 3/0238* (2013.01); *B01D 2252/204* (2013.01); *B01D 2253/104* (2013.01); *B01D 2257/2025* (2013.01); *B01D 2257/302* (2013.01); *B01D 2257/406* (2013.01); *F25J 2205/30* (2013.01); *F25J 2205/50* (2013.01); *F25J 2205/60* (2013.01); *F25J 2210/12* (2013.01); *F25J 2215/62* (2013.01); *F25J 2245/02* (2013.01)

(58) Field of Classification Search
CPC ........ B01D 2257/406; B01D 2257/302; B01D 2257/2025; B01D 2252/204; B01D 2256/245; B01D 2256/16; F25J 3/0238; F25J 2205/60; F25J 2205/50; F25J 2205/30; F25J 2245/02; F25J 2215/62; F25J 2210/12
See application file for complete search history.

(56) References Cited

U.S. PATENT DOCUMENTS

| | | | |
|---|---|---|---|
| 8,066,868 | B1 | 11/2011 | Zimmermann |
| 9,011,578 | B2 | 4/2015 | Hickey et al. |
| 10,308,733 | B2 | 6/2019 | Al-Shammari et al. |
| 2004/0247509 | A1 | 12/2004 | Newby |
| 2012/0053383 | A1 | 3/2012 | Malaty et al. |
| 2019/0367428 | A1* | 12/2019 | Ramamurthy ............ C07C 4/06 |
| 2019/0367430 | A1 | 12/2019 | Bruder et al. |
| 2020/0087143 | A1 | 3/2020 | Chaubet et al. |

OTHER PUBLICATIONS

Search Report issued during prosecution of corresponding French Patent Application No. FR2106391 on Feb. 8, 2022. (2 pages).

* cited by examiner

PROCESS FOR TREATING A GAS STREAM FROM PLASTIC PYROLISIS AND/OR BIOMASS PYROLISIS, AND INSTALLATION FOR INTEGRATION INTO A STEAM CRACKER

CROSS-REFERENCE TO RELATED APPLICATIONS

This application claims priority to and the benefit of French Patent Application No. FR 21 06391, filed Jun. 16, 2021, the entire contents of which are herein incorporated by reference in their entirety.

FIELD

The present invention concerns a process for treating at least one gas stream derived from pyrolysis of plastic and/or biomass.

BACKGROUND

Environment protection requirements have prompted industrialists to make provision for plastic waste treatment channels, or/and for biomass recovery channels, in particular to produce fuels from renewable resources.

These channels use pyrolysis to treat plastic materials and/or biomass to obtain recoverable products.

Gases from pyrolysis contain a large number of compounds having high added value (HAV) able to be given reuse.

This is particularly the case for hydrocarbon compounds such as ethylene, propylene, butadiene, benzene, toluene, paraffins and hydrogen.

However, these gases derived from the pyrolysis of plastic and/or biomass cannot be given direct use for routing towards crackers or self-contained olefin production units. Plastic and/or biomass which has undergone pyrolysis contains impurities which are directly found or degraded in pyrolysis gases.

This includes sulfur-containing compounds for example such as mercaptans, sulfur oxides or hydrogen sulfide, acid gases such as hydrochloric acid or hydrocyanic acid, carbon monoxide, carbon dioxide, oxygen and oxygen derivatives, ammonia, nitrogen oxides and other nitrogen- or chlorine-derived compounds, metals. These contaminants can cause safety and/or operability risks in the steam cracker or self-contained olefin recovery unit. In many cases, pyrolysis gases are therefore not reused for the recovery of HAV products but are routed towards other units such as energy-producing units.

U.S. Pat. No. 9,011,578 proposes a solution concerning the use in a downstream fermentation unit of some compounds contained in the gases derived from pyrolysis of biomass.

Before the gases are fed into the fermentation unit, they are are purified via a treatment process which removes some compounds.

Said process is efficient for obtaining gases compatible with fermentation, but does not allow recovery of hydrocarbons for reuse thereof.

SUMMARY OF THE INVENTION

It is one object of the invention to provide a process allowing highly efficient treatment of pyrolysis gases, in particular pyrolysis gases of plastic and or biomass material, for the purpose of recovering some compounds contained in these pyrolysis gases, and olefins in particular.

For this purpose, the subject of the invention is a treatment process of the aforementioned type, characterized by the following steps:

- quenching and washing with water the gas streams derived from pyrolysis of plastic and/or biomass in a quench/wash unit, and separating an aqueous phase from a washed gas stream;
- compressing then cooling the washed gas stream to form a compressed gas stream;
- washing the compressed gas stream under pressure to form a washed gas stream;
- passing the washed gas stream through at least one acid removal unit to form an acid-depleted gas stream;
- drying the acid-depleted gas stream to form a dry gas stream;
- passing the dry gas stream through at least one impurity removal unit to form a purified gas stream;
- feeding the purified gas stream into a cryogenic absorption unit and supplying the cryogenic absorption unit with a hydrocarbon cryogenic solvent to obtain a light gas residue at a first outlet of the cryogenic absorption unit, and a $C_2^+$ hydrocarbon fraction at a second outlet of the cryogenic absorption unit The process of the invention may comprise one or more of the following characteristics taken alone or in any technically possible combination:

- the gas stream derived from pyrolysis contains $C_2^+$ hydrocarbons and light compounds such as hydrogen and/or methane;
- the gas stream derived from pyrolysis contains carbon monoxide, carbon dioxide, nitrogen oxides, and/or oxygen and derivatives of oxygen particularly alcohols, aldehydes and/or ketones, nitrogen-containing compounds such as nitrogen and ammonia and/or acid compounds such as hydrochloric acid and hydrocyanic acid, chlorine derivatives and/or sulfur-containing compounds in particular mercaptans, carbon oxysulfides, and hydrogen sulfide;
- the hydrocarbon cryogenic solvent comprises $C_3$ and/or $C_4^+$ hydrocarbons, in particular $C_3$ hydrocarbons;
- it comprises a step of separating the $C_2^+$ hydrocarbon fraction into a $C_2$ hydrocarbon fraction and into at least one $C_3^+$ hydrocarbon fraction, at least part of said $C_3^+$ hydrocarbon fraction being recycled in the cryogenic absorption unit;
- the separation step comprises the production of a $C_3$ hydrocarbon fraction and $C_4^+$ hydrocarbon fraction, at least part of the $C_3$ hydrocarbon fraction being recycled in the cryogenic absorption unit;
- the light gas residue contains fuel gas, in particular methane, hydrogen, and light compounds of the purified gas stream such as carbon monoxide, nitrogen, nitrogen monoxide and/or oxygen;
- the light gas residue is intended to be routed into a cracking unit, in particular into the combustible gas network of a steam cracker and/or is intended to form a fuel gas;
- the at least one acid removal unit comprises an amine unit and/or caustic wash unit, the compressed gas stream passing through the amine unit or/and caustic wash unit;
- the impurity removal unit comprises at least one activated metal bed, in particular an activated alumina bed or mixed adsorbent; the sulfur-containing compounds in particular hydrogen oxysulfide and mercaptans, and/or ammonia, nitrogen-containing compounds, chlorine-containing compounds, oxygen-containing compounds in particular alcohols, and/or silicones contained in the dry gas stream being retained on the at least one activated metal bed;

at least part of the $C_2^+$ hydrocarbon fraction is fed into a cracker able to produce an ethylene fraction, or into a self-contained unit able to produce an ethylene fraction;

at least part of the aqueous phase produced at the quench/wash step is pressurized and placed in contact with the compressed gas stream at the high-pressure wash step;

at least two streams from among the stream of purified gas, the hydrocarbon cryogenic solvent, the light gas residue, and/or at least one reflux or condensate of the cryogenic absorption unit are placed in heat exchange contact in a cold box formed in particular of a single item of plate-fin cryogenic equipment particularly in brazed aluminium;

the steps to quench and wash with water the gas stream derived from pyrolysis, to compress and cool the washed gas stream, to wash the compressed gas stream under pressure, to pass the washed gas stream through at least one acid removal unit, to dry the acid-depleted gas stream, to pass the dry gas stream through at least one impurity removal unit, to feed the purified gas stream into a cryogenic absorption unit are successively carried out in the indicated order.

A further subject of the invention is an installation for treating at least one gas stream derived from pyrolysis of plastic and/or biomass, characterized by:

a quench/wash unit, able to quench and wash with water the gas stream derived from pyrolysis of plastic and/or biomass, and to separate an aqueous phase from a washed gas stream;

a compression/cooling unit of the washed gas stream to form a compressed gas stream;

a high-pressure wash unit of the compressed gas stream to form a washed gas stream;

at least one unit to remove acids contained in the washed gas stream to form an acid-depleted gas stream;

a drying unit of the acid-depleted gas stream to form a dry gas stream;

at least one unit to remove impurities in the dry gas stream to form a purified gas stream;

a cryogenic absorption unit able to be fed with the purified gas stream and supplied with a hydrocarbon cryogenic solvent to obtain a light gas residue at a first outlet of the cryogenic absorption unit, and a $C_2^+$ hydrocarbon fraction at a second outlet of the cryogenic absorption unit The installation of the invention may comprise one or more of the following characteristics taken alone or in any technically possible combination:

an outlet of the quench/wash unit recovering the aqueous phase is linked to an inlet of the high-pressure wash unit, a compressing member of the aqueous phase being interposed between the outlet of the quench/wash unit and the inlet of the high-pressure wash unit;

the cryogenic absorption unit comprises a cold box formed in particular of a single item of plate-fin cryogenic equipment particularly in brazed aluminium able to place in heat exchange contact at least two streams from among the purified gas stream, hydrocarbon cryogenic solvent, light gas residue and/or at least one reflux or condensate of the cryogenic absorption unit.

BRIEF DESCRIPTION OF THE DRAWINGS

The invention will be better understood on reading the following description given solely as an example and with reference to the appended Figures in which.

DETAILED DESCRIPTION

In the remainder hereof, the term «$C_n$ hydrocarbons» means that the number of carbon atoms contained in the hydrocarbon is n. The term «$C_n^+$ hydrocarbons» means that the number of carbon atoms contained in the hydrocarbon is higher than or equal to n.

For example, the term $C_2$ hydrocarbons particularly comprises ethane, ethylene and acetylene. The term $C_2^+$ hydrocarbons comprises hydrocarbons having a number of carbon atoms higher than or equal to 2, for example ethane propane, butane, pentane etc. . . . .

In the remainder hereof pressures are relative pressures, and the compositions expressed as a percentage are weight percentages unless otherwise stated.

Also, a same reference number can designate a flow circulating in a pipe or the pipe by which it is conveyed.

The term «atmospheric pressure» designates the pressure of ambient air mass at the installation site. This pressure is generally between 900 mbar and 1100 mbar absolute.

Figure 1:
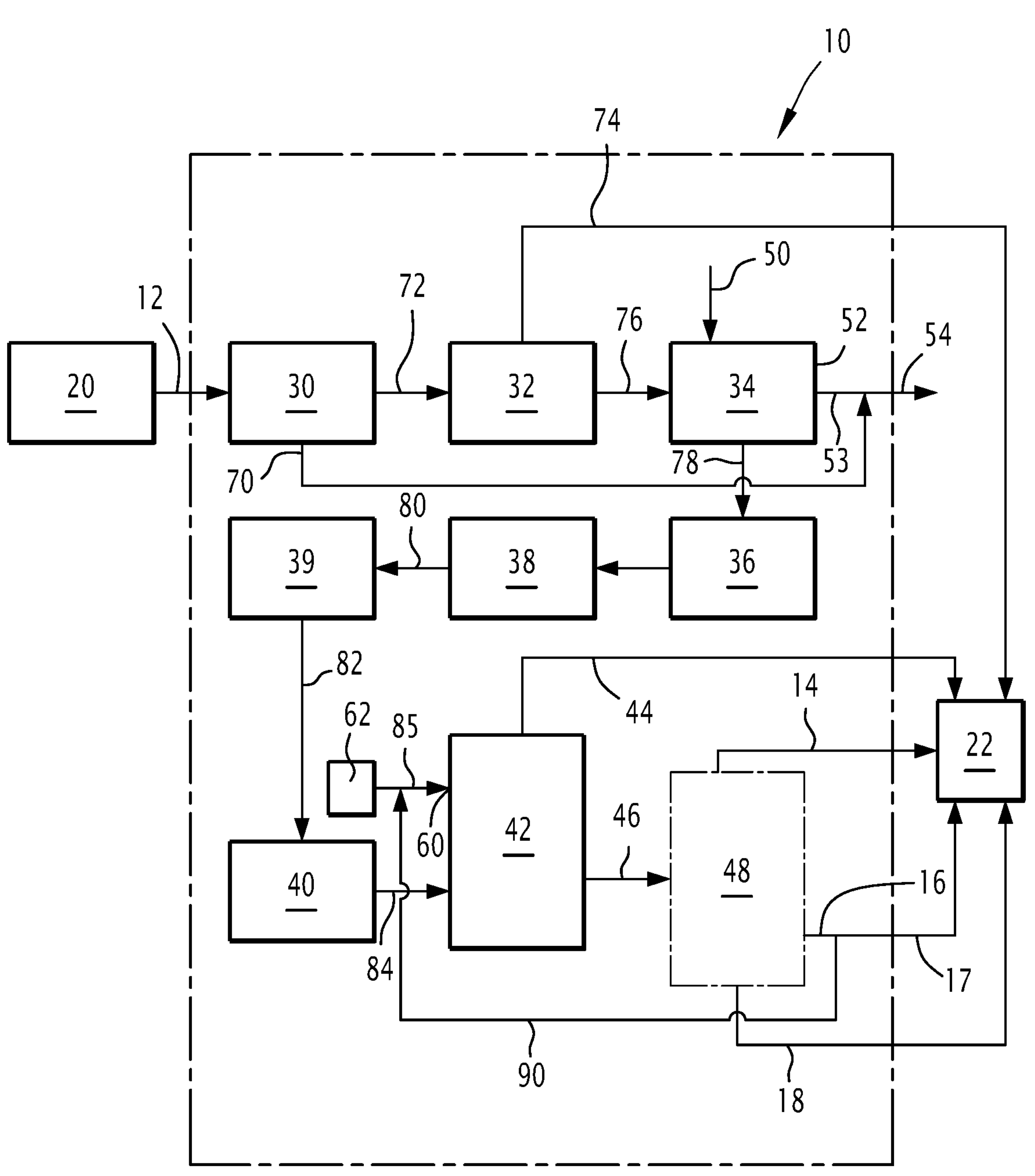
FIG. 1 is a block diagram illustrating an installation for implementing a first purification process of the invention, intended in particular to produce a $C_2$ hydrocarbon fraction recoverable in a steam cracker or self-contained ethylene production unit.

A first installation 10 for treating a gas stream 12 derived from pyrolysis of plastic material or/and pyrolysis of biomass is illustrated in FIG. 1.

This installation 10 is intended for implementation of a first process for treating the gas stream 12, to form at least one fraction 14 of $C_2$ hydrocarbons intended to be routed towards a back-end installation 22. For example, the back-end installation 22 is the recovery section of a steam cracker.

The gas stream 12 is treated at various steps and fractionated into several fractions which feed the steam cracker downstream of the cracking furnaces.

The installation 10 of the invention allows the integration of fractions produced in steam crackers having various fractionating designs: it can be a steam cracker having a front-end demethanizer combined with a back-end hydrogenation unit.

As a variant, the steam cracker has a front-end deethanizer or front-end depropanizer combined with a front-end hydrogenation unit.

In a further variant, the back-end installation 22 is a self-contained olefin recovery unit intended to produce ethylene from fraction 14 of $C_2$ hydrocarbons. The self-contained unit can also be intended to produce propylene from a fraction 17 of $C_3$ hydrocarbons optionally obtained in the installation 10.

The gas stream 12 is produced in a pyrolysis installation 20 of plastic material and/or biomass positioned upstream of the treatment installation 10 of the invention.

The pyrolysis installation 20 is particularly intended to carry out chemical decomposition of the plastic material and/or biomass at high temperature, in the absence of oxygen, or in an oxygen-depleted atmosphere, to prevent oxidation and combustion.

For example, pyrolysis is conducted in at least one reactor of installation 20, at a temperature higher than 500° C. The targeted oxygen content is the lowest possible, the residual content only being associated with non-controllable air input phenomena, such as those potentially induced by the fact that the plastic waste and/or biomass is fed into the reactor via a screw conveying system operating in ambient air. However, this oxygen content is largely lower than that of ambient air.

Pyrolysis generally produces solid pyrolysis residues including coke and ash, and at least one pyrolysis gas forming all or part of the gas stream 12. Pyrolysis can also produce liquids, in particular pyrolysis liquids and particularly oils.

Concerning the pyrolysis of plastic material, the plastic materials are waste plastics for example. They then comprise at least one polymer such as polyethylene, polypropylene, polystyrene, etc., which can be mixed with biogenic residues such as paper, food or green residues, cotton, . . . .

Concerning the pyrolysis of biomass, the biomass is formed for example of organic matter of plant, animal, bacterial or fungal origin.

For example, the biomass is lignocellulosic biomass such as wood, green residues, straw, sugar-cane pulp, fodder, carbohydrate biomass such as cereals, sugar-beet, sugar cane or/and oil-containing biomass such as rapeseed, palm, etc.

The gas stream 12 intended to be treated in the treatment installation 10 comprises light compounds for example on entering the installation 10 such as methane and at least one recoverable compound selected from among $C_2$ hydrocarbons, $C_3$ hydrocarbons, $C_4$ hydrocarbons, benzene toluene, hydrogen.

For example, the gas stream 12 intended to be treated in the installation 10 comprises (on wet basis) between 10 weight % and 20 weight % of $C_2$ hydrocarbons, between 2 weight % and 10 weight % of $C_3$ hydrocarbons, between 1 weight % and 5 weight % of $C_4$ hydrocarbons, between 2 weight % and 10 weight % of (benzene+toluene) and between 0.3 weight % and 4 weight % of hydrogen.

The gas stream 12 generally comprises a large amount of water, in particular an amount of water higher than 30 weight %.

Since the gas stream 12 is obtained by pyrolysis of plastic material and/or biomass, it also comprises various compounds or/and impurities which are not usable or desirable in the back-end installation 22.

For example, the gas stream 12 comprises carbon monoxide, carbon dioxide, nitrogen oxides and/or oxygen and oxygen derivatives (alcohols, aldehydes, ketones, . . . ).

It comprises for example (on wet basis) between 2 weight % and 20 weight % of carbon monoxide, between 3 weight % and 20 weight % of carbon dioxide.

The gas stream 12 may possibly comprise nitrogen-containing compounds such as nitrogen and ammonia and/or acid compounds such as hydrochloric acid, hydrocyanic acid and/or various other chlorine derivatives such as dioxins and furans. For example (on dry basis) it comprises between 500 ppmV and 1500 ppmV of ammonia, between 5000 ppmV and 150 000 ppmv of nitrogen, between 50 ppmV and 5000 ppmV of hydrochloric acid and between 100 ppmV mol and 200 ppmV of hydrocyanic acid.

The gas stream 12 also possibly comprises sulfur-containing compounds such as hydrogen sulfide, carbon oxysulfides, mercaptans and thiophenes.

The content (on dry basis) of hydrogen sulfide is between 200 ppmV and 1000 ppmV for example, those of carbon oxysulfides and thiophene being between 5 ppmV and 100 ppmV, and that of mercaptans between 1 ppmV and 100 ppmV.

The temperature of the gas stream 12 is generally higher than 80° C. on entering the installation 10.

The pressure of the gas stream 12 on entering the installation 10 is for example slightly higher than atmospheric pressure e.g. between 1100 mbar and 3000 mbar absolute.

All the aforementioned compounds are advantageously in gaseous form on entering the installation 10. Via liquid entrainment or via volatility, the gas stream 12 may also comprise metals, dust and/or tars.

With reference to FIG. 1, the installation 10 comprises a low-pressure quench/wash unit 30, a compression/cooling unit 32 and a high-pressure wash unit 34.

The installation 10 in this example further comprises acid removal units 36, 38, in particular an amine unit 36 and caustic wash unit 38.

Downstream of the acid removal units 36, 38, the installation 10 also comprises a drying unit 39, an impurity removal unit 40, and downstream of the impurity removal unit 40 a cryogenic absorption unit 42 intended for the production of a light gas residue 44 and fraction 46 of $C_2^+$ hydrocarbons.

The installation 10 may further advantageously comprise a unit 48 for fractionating the fraction 46 of $C_2^+$ hydrocarbons, to form hydrocarbon fractions 14, 16, 18, in particular fraction 14 of $C_2$ hydrocarbons intended for the back-end installation 22, fraction 16 of $C_3$ hydrocarbons intended to be at least partly recycled in the cryogenic absorption unit 42 and a fraction 18 of $C_4^+$ hydrocarbons The quench/wash unit 30 comprises at least one quench/wash capacity for example, and at least one water injector to inject water in liquid form into the capacity. The injected water is intended for cooling of the gas stream 12 and partial condensing thereof to recover an aqueous phase 70.

The compression/cooling unit 32 comprises at least one compressor, most often a multi-stage compressor provided with inter-stage cooling, in particular water or air cooling.

The high-pressure wash unit 34 advantageously comprises at least one inlet 50 to inject pressurized water, at least one wash chamber 52 intended to receive the pressurized water and at least one outlet 53 to evacuate the pressurized water from the chamber 52.

The amine unit 36, as is conventional, comprises an absorber and regenerator. In the absorber, a downflow of amines meets a gas upflow and receives the acid gases contained in the gas stream. The sweetened gas stream leaves the absorber with reduced acid content. The flow of amines enriched with acids is evacuated towards the regenerator. A flash vessel is usually installed between the absorber and regenerator. To limit hydrocarbon losses, the gas stream resulting from this step can be recycled in the compression unit 32.

In the regenerator, the flow of amines enriched with acids is heated and routed to an evaporator to evacuate acid-rich vapours. The flow of amines re-depleted of acids is cooled by the enriched flow of amines leaving the absorber, and is returned into the absorber.

The caustic wash unit 38 comprises at least one capacity provided with an inlet to supply caustic soda solution to wash the gas stream with sodium hydroxide.

The drying unit 39 usually comprises a propylene cooler, followed by a liquid/vapour separator the headstream of which is passed through molecular sieve beds of size 3 Angström in particular. The drying unit 39 is able to remove the water contained in the gas stream whilst not trapping the olefins contained in the gas stream. The unit 39 may also comprise a mercury reduction function.

The impurity removal unit 40 is able to provide additional protection with regard to the removal in particular of ammonia and other nitrogen-containing compounds, chlorine-containing compounds, sulfur-containing compounds, alcohols, water. For example, it comprises active bed adsorbents, in particular active metal beds such as beds of active alumina or other mixed adsorbents.

The cryogenic absorption unit 42 comprises at least one cryogenic absorption column, an inlet 60 to feed solvent and a source 62 of fresh solvent.

The source 62 is able to supply replenishing solvent.

The solvent is composed of liquid hydrocarbons for example, in particular liquid $C_3^+$ hydrocarbons and particularly liquid propane.

By «cryogenic» it is meant that the temperature of the solvent 85 and of the gas stream 84 fed into the cryogenic absorption column is lower than −20° C., in particular between −30° C. and −40° C.

The absorption column intended to place the gas stream in contact with the solvent can be equipped with plates or packing.

The fractionating unit 48 which is optional comprises at least one distillation column, in particular at least one first distillation column able to separate the fraction 14 of $C_2$ hydrocarbons at the head of the column from at least one $C_3^+$ hydrocarbon fraction produced at the foot of the column.

It advantageously comprises a second distillation column, able to treat the $C_3^+$ hydrocarbon fraction to form fraction 16 of $C_3$ hydrocarbons and fraction 18 of $C_4^+$ hydrocarbons recovered at the foot of the second distillation column.

A first process for treating a gas stream 12 derived from the pyrolysis installation 20 is now described.

Initially, the gas stream 12 having the composition such as described above, is produced by the pyrolysis installation 20. It generally has a temperature higher than 80° C., and pressure of between 1100 mbar and 3000 mbar absolute.

As indicated above, the gas stream 12 generally contains a large amount of water vapour in particular more than 30 weight % of water.

The gas stream 12 is fed into the quench/wash unit 30. It is placed in direct contact with the low-pressure wash water to obtain quenching of the gas stream 20 and at least partial condensing of the water contained in the gas stream 20.

The operating pressure in the water quench/wash column 30 is lower than 2 bar, in particular at the pressure of the gas stream 12 from which in-line head loss is deducted i.e. a pressure slightly higher than atmospheric pressure.

The temperature of the wash water fed into the quench/wash unit 30 is determined by site conditions. For example, if the temperature of cooling water available on site is 35° C., a typical temperature for the wash water is 37 to 40° C.

At the foot of the quench/wash column 30, an aqueous phase corresponding to the wash water and part of the water contained in the gas stream 20 is recovered.

The wash water after cooling is returned to the head of the column while the part corresponding to condensed water is extracted. It forms an aqueous phase 70 which is therefore recovered separately from the cooled and washed gas stream 72 formed in the quench/wash unit 30.

Advantageously, the aqueous phase 70 comprises more than 85% of the water contained in the gas stream 12 fed into the quench/wash unit. The cooled and washed gas stream 72 typically contains less than 10 weight % of water.

Washing in the quench/wash column 30 allows a reduction in water-soluble compounds such as ammonia, alcohols or hydrochloric acid. Advantageously, the wash water can be acidified to amplify this function. Washing also allows a reduction in potential contents of metal, dust and/or tars contained in the stream 12.

The washed gas stream 72 is recovered at a temperature set by site conditions. For example, if the temperature of the cooling water available on site is 35° C., a typical temperature of the washed gas stream 72 is 40° C. to 45° C. The washed gas stream 72 is then routed to the compression/cooling unit 32 to be compressed at a pressure higher than 10 bar, in particular between 20 bar and 30 bar.

At each compression stage, the gas stream 72 is cooled in a coolant to a temperature set by site conditions e.g. 40° C. Advantageously final cooling with propylene coolant can be implemented to reduce the temperature of the stream 76, for example to between 15° C. and 20° C. and thereby further optimise recovery of condensates.

A hydrocarbon condensate 74 is recovered. This condensate (on dry basis) particularly contains benzene (for example between 60 weight % and 80 weight %), toluene (for example between 15 weight % and 25 weight %), $C_4$ hydrocarbons (for example between 5 weight % and 15 weight %), $C_3$ hydrocarbons and lighter (typically less than 5 weight %), $C_5$ hydrocarbons (typically less than 2 weight %) and traces of dissolved gases, water, impurities such as sulfur-containing or other compounds.

Fraction 74 is advantageously sent to the back-end installation 22, to allow extraction of compounds of commercial value e.g. benzene, toluene and butadiene.

A compressed gas stream 76 is formed at the outlet of the compression/cooling unit 32. The compressed gas stream 76 is fed into the high-pressure wash unit 34. It is placed in contact with the pressurized wash water arriving from inlet 50 at a pressure higher than 10 bar (advantageously higher than 20 bar) and at a temperature advantageously higher than 45° C.

Washing of the compressed gas stream 76 reduces the quantity of hydrocyanic acid in the compressed gas stream 76. Unlike low-pressure washing 30 which recirculates the water, this high-pressure washing is advantageously performed with one-through circulating water to maximise removal of hydrocyanic acid. Advantageously more than 75% of the hydrocyanic acid contained in the compressed gas stream 76 is recovered in the outgoing pressurized water at outlet 53.

The washed gas stream 78 at the outlet of the high-pressure wash unit 34 therefore has a hydrocyanic acid content which depends on the amount contained in the gas stream 12, hence on the type of waste being fed into the pyrolysis unit 20. For example, the content is between 50 ppmV and 500 ppmV.

High-pressure washing also allows higher specifications to be reached regarding the impurities already reduced in the low-pressure wash 30. The contents of ammonia and hydrochloric acid in stream 78 are for example less than 2 ppmV and 1 ppmV respectively.

The washed gas stream 78 is then successively sent through each acid removal unit 36, 38.

In these units, it is successively placed in contact with the amine flow and with sodium hydroxide for removal in particular of carbon dioxide and hydrogen sulfide contained in the washed gas stream 78.

Operating costs of the amine unit can especially be generated by amine degradation products fostered by the presence in the stream 78 of oxygen-containing compounds and residual hydrocyanic acid. To reduce these costs, the amine unit 36 may comprise specificities such as the presence of a reclaimer and/or ion exchange bed systems.

Advantageously, the carbon dioxide and hydrogen sulfide contained in the washed gas stream 78 are removed in units 36, 38 so that the gas stream depleted of acids 80 leaving the outlet of units 36, 38 preferably comprises less than 0.5 ppmV of carbon dioxide and preferably less than 0.1 ppmV of hydrogen sulfide.

Advantageously, the amine and caustic washing in units 36 and 38 also allows a reduction in residual hydrocyanic acid and partial reduction of some sulfur-containing compounds such as mercaptans.

The gas stream depleted of acids 80 is fed into the drying unit 39 where the water content thereof is reduced. A dry gas stream 82 is thus formed.

The dry gas stream 82 advantageously has a water content of less than 1 ppm by weight. Unit 39 can also advantageously comprise a mercury reducing function, down to typical contents of below 10 ng/$NM^3$.

The dry gas stream 82 is next routed to the impurity removal unit 40 for additional protection regarding the removal in particular of ammonia and other nitrogen-containing compounds and/or chlorine-containing compounds and/or sulfur-containing compounds (particularly hydrogen oxysulfide and mercaptans), and/or oxygen-containing compounds (alcohols in particular) to form a purified gas stream 84. Unit 40 may also allow a reduction in other impurities (e.g. silicone). For example, it comprises active bed adsorbents, in particular active metal beds such as active alumina beds or other mixed adsorbents arranged in series.

The total impurity content in the purified gas stream 84 is preferably less than 1 ppm by weight.

The purified gas stream 84 is afterwards routed to the cryogenic absorption unit 42. It is first cooled to cryogenic temperature then placed in contact with a cold hydrocarbon solvent 85 in a cryogenic absorption column. The absorption column intended to contact the gas stream with the solvent can be equipped with plates or packing.

The hydrocarbon solvent 85 is cooled to cryogenic temperature then fed via inlet 60 into the absorption column. The hydrocarbon solvent 85 is formed of solvent supplied by the solvent replenishment source 62 and optionally from recycled solvent derived from the fractionating unit 48.

As indicated above, the hydrocarbon solvent 85 comprises $C_3$ hydrocarbons and/or $C_4^+$ hydrocarbons. Preferably, it comprises more than 50 mole % of $C_3$ hydrocarbons and advantageously more than 90 mole % of $C_3$ hydrocarbons, propane in particular.

The temperature of the hydrocarbon cryogenic solvent 85 here is lower than −20° C., and is advantageously between −30° C. and −40° C. The pressure of the cryogenic absorption column is usually between 15 bar and 25 bar.

The hydrocarbon solvent 85 is advantageously fed into the head of the absorption column and circulates in counter-flow to the purified gas stream 84 fed into the cryogenic absorption unit 42 at the foot of the absorption column.

Therefore, the $C_2^+$ hydrocarbons contained in the purified gas stream 84 are collected by the hydrocarbon solvent 85 and are recovered in the form of a fraction 46 of $C_2^+$ hydrocarbons at the foot of the absorption column. On the contrary, the residual gases form the light gas residue 44 recovered at the head of the cryogenic absorption unit.

Reboiling of the absorption column can be carried out for example with low-pressure steam (e.g. at a pressure lower than 5 bar) to maintain the methane specification in fraction 46 of $C_2^+$ hydrocarbons.

Optionally, the absorption column can be equipped with one or more intermediate circulating refluxes to improve absorption efficiency of the compounds having high added value in the solvent. Usually, the intermediate circulating refluxes are cooled to a temperature advantageously of between −30° C. and −40° C. before being reinjected into the column.

To limit solvent losses in the headstream of the absorption column, the solvent is usually directed towards a partial condensation step. The liquid formed is returned to the stream of solvent 85 while the light gas residue 44 (fuel gas stream) is expanded, reheated to ambient temperature and returned to the fuel network of the steam cracker.

Advantageously, several thermal integrations cited in this process can be combined in a single item of plate-fin cryogenic equipment in brazed aluminium (called «cold box»), which optimises the cost of the unit and recovery of energy. For example, cooling of the purified gas stream 84, cooling of the solvent 85, heating of the light gas residue 44, cooling of the circulating reflux(es) of the cryogenic absorption column and/or partial condensing of the cryogenic absorption column can be conducted in the same item of equipment.

The $C_2^+$ hydrocarbon fraction 46 preferably contains more than 99.5% of the $C_2$ hydrocarbons contained in the purified gas stream 84.

The light gas residue 44 advantageously contains fuel gas in particular methane, hydrogen, and the other light compounds of the purified gas stream 84 such as carbon monoxide and nitrogen. It contains hydrocarbon compounds essentially derived from the solvent 85, and $C_2$ hydrocarbons present in the purified gas stream 84 and not recovered in fraction 46. Finally, the light residue 44 may also contain light impurities of fraction 46 such as nitrogen oxide, oxygen and/or argon as well as other impurities via volatility such as light sulfur-containing compounds or ammonia.

In particular, the light gas residue 44 contains the nitrogen oxide and oxygen contained in the purified gas stream 84. Therefore, the content of these compounds in fraction 46 of $C_2^+$ hydrocarbons, lies below detection limits. Additionally, this fraction 46 contains very small amounts of light products. For example, the content of methane in relation to ethylene can be lower than or equal to 500 molar ppm. This guarantees the methane specification in ethylene without additional fractionating.

In this manner, the fraction 46 of $C_2^+$ hydrocarbons (and by extension the fractions derived therefrom e.g. fractions 14, 17, 18) are able to be integrated into a fractionating section of the steam cracker while avoiding hazards related to the presence of nitrogen oxides.

Indeed, when gases having a combined content of nitrogen oxide, oxygen, dienes and/or ammonia are brought to low temperature, in particular to temperatures lower than −100° C., NOx gums or salts can be formed. These compounds have a risk of exploding when brought to ambient temperature. The purified gas stream 84 cannot therefore be brought to low temperature, in particular to the temperatures usually encountered at the cold ends of steam cracker cold boxes. In particular, the mixture of the purified gas stream 84 with cracked gases derived from a steam cracker having a front-end demethanizer would not guarantee the safety of the installation, since the combined stream would be brought to temperatures lower than −100° C. before being fed into the demethanizer.

The coldest temperature encountered in the cryogenic absorption unit 42 is limited to the temperatures which can be reached when propylene is used as coolant. This temperature is always higher than or equal to the equilibrium temperature of propylene at atmospheric pressure (−47° C.). This obviates the risk of explosion of these gums or salts when they are reheated.

The process of the invention most efficiently removes nitrogen monoxide, oxygen and ammonia, in particular when it is not possible carry out removal of nitrogen oxides and oxygen using a catalyst of deoxygenation type on account of the high content of carbon monoxide and diolefin compounds in the gas stream 12.

In addition, the process of the invention is most useful for integrating the stream 84 in a steam cracker designed as a front-end deethanizer or front-end depropanizer combined with a front-end hydrogenation unit. The problem described above relating to nitrogen oxide is minimised since with this design only the light part having undergone hydrogenation is brought to temperatures lower than −100° C. However, in this design, the acetylene converter is highly sensitive to runaway when fluctuations occur in carbon monoxide content.

The fraction 46 of $C_2^+$ hydrocarbons (and by extension the fractions derived therefrom e.g. fractions 14, 17, 18) being free of carbon monoxide, the risk of such runaway is limited and integration of these fractions upstream of the hydrogenation converter is made safe.

Also, as discussed above, the process of the invention guarantees heed of methane specifications of ethylene whilst maintaining scarcely demanding cryogenic conditions through the use of a single cryogenic absorption unit 42, which is advantageous in particular when the back-end installation 22 is a self-contained olefin recovery unit.

The fraction 46 of $C_2^+$ hydrocarbons produced in the cryogenic absorption unit 42 is fed into the fractionating unit 48 when provided.

In the first distillation column of the fractionating unit 48, the fraction 14 of $C_2$ hydrocarbons is recovered at the head.

This fraction 14 contains more than 99% of the $C_2$ hydrocarbons contained in fraction 46 of $C_2^+$ hydrocarbons. It usually contains more than 99.5 mole % of $C_2$ hydrocarbons, ethylene in particular.

Fraction 14 is then routed to the back-end installation 22 as described above.

A flow of $C_3^+$ hydrocarbons is formed at the foot of the first distillation column. This flow is preferably led into a second distillation column to separate fraction 16 of $C_3$ hydrocarbons from fraction 18 of $C_4^+$ hydrocarbons.

Fraction 16 of $C_3$ hydrocarbons generally contains the $C_3$ hydrocarbons present in the purified gas stream 84 and those in the solvent 85. A solvent recycling flow 90 is formed from at least part of fraction 16 of $C_3$ hydrocarbons.

The recycling flow 90 is recycled towards the solvent feed inlet 60 to form part of the solvent fed into the cryogenic absorption unit 42. This limits solvent replenishment 85 from source 62. Also, the residual part 17 of flow 16 is led into the back-end installation 22 for recovery of propylene in particular.

A fraction 18 of $C_4^+$ hydrocarbons is recovered at the foot of the second distillation column. It is advantageously directed to the back-end installation 22 to allow the extraction of compounds having commercial value e.g. butadiene, benzene and toluene.

The process of the invention therefore efficiently removes the contaminants contained in the gas stream 12 derived from pyrolysis of plastic and/or biomass, which could compromise integration of the stream in a downstream installation of steam cracker type (or other olefin recovery unit). They often comprise compounds generating safety risks for these installations, risks regarding quality of end products and/or poisoning of catalysts contained in these installations.

It is therefore possible to produce a purified gas stream 84 free of these contaminants. In addition, separation of the light gas residue 44 produces a residue which can be integrated in downstream processes for example as fuel or for the recovery of hydrogen.

For example, the nitrogen monoxide contained in gas stream 12 is efficiently removed in the cryogenic absorption unit 42, limiting risks of the formation of nitrogen oxide gums or salts at subsequent steps.

The removal of carbon monoxide from the gas residue 44 also avoids fluctuations in carbon monoxide content in fraction 46 of $C_2^+$ hydrocarbons (and by extension in the fractions derived therefrom e.g. fractions 14, 17, 18), to reduce the risk of reaction runaway in the acetylene hydrogenation reactors of some steam cracker units (or self-contained olefin recovery unit).

Therefore, the fraction 46 of $C_2^+$ hydrocarbons produced in the installation 10 (and by extension the fractions derived therefrom e.g. fractions 14, 17, 18), is able to be used directly in steam cracking units or can be recovered in the form of an end product in a self-contained olefin production unit.

The description of the number and arrangement of the fractionating columns of unit 48, and tapping of the recycling flow 90 discussed above, corresponds to a case in which the fresh solvent used mostly contains $C_3$ hydrocarbons. Depending on the solvent used and size of the unit, variants can be envisaged.

Figure 2:
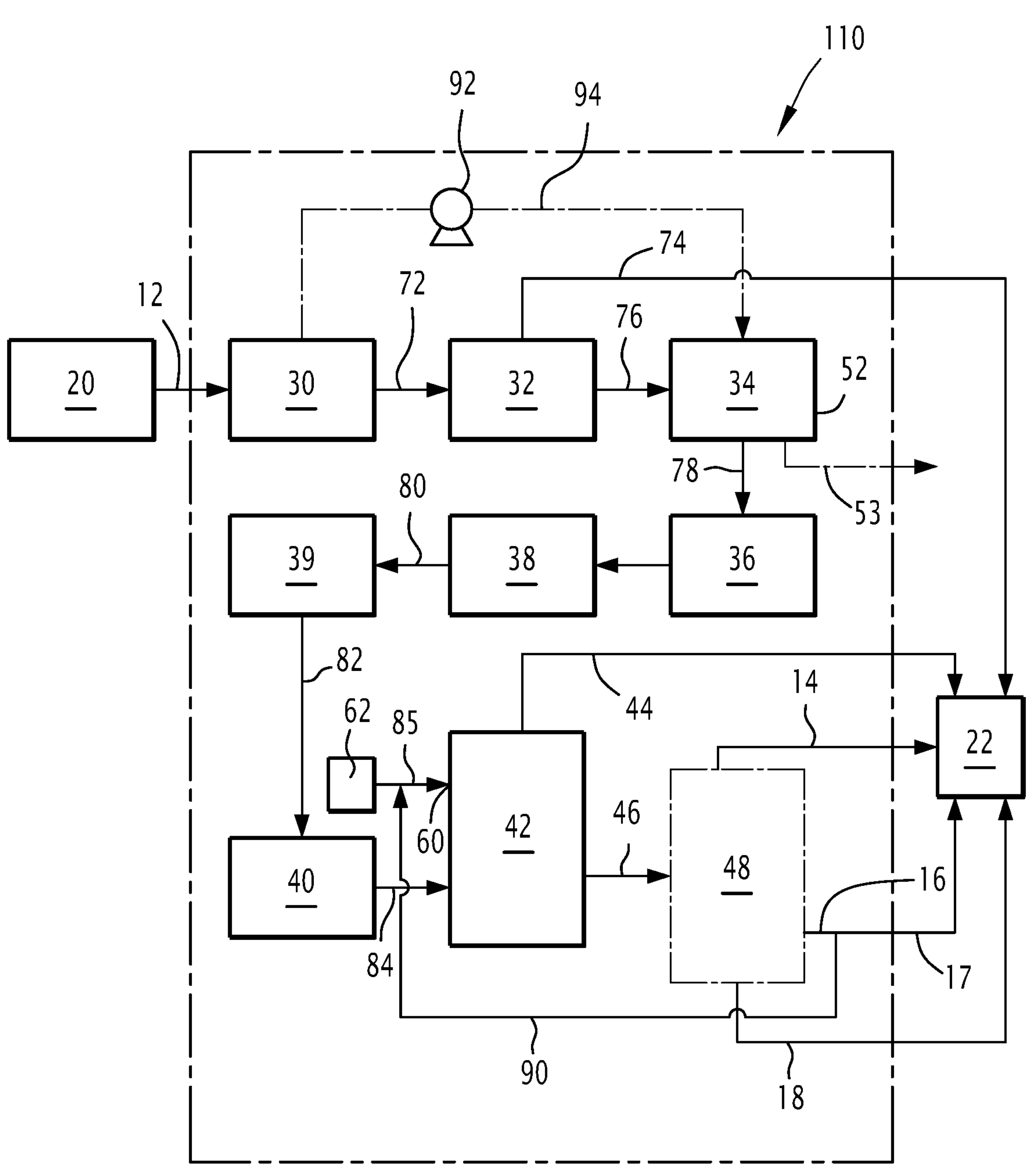
FIG. 2 is a variant of the installation intended for the implementation of a second purification process of the invention.

In the variant of installation 110 illustrated in FIG. 2, the aqueous phase 70 derived from the quench/wash unit 30 is recovered and routed to a compressing member 92 which here is a pump.

The aqueous phase 70 is pumped up to the required pressure to carry out high-pressure washing, a pressure advantageously higher than 20 bar, to form a compressed aqueous phase 94.

The compressed aqueous phase 94 is led into the high-pressure washing chamber 52 of the high-pressure wash unit 34. It is contacted with the compressed gas stream 76 to allow high-pressure washing of the compressed gas stream 76.

Similar to the installation 10 in FIG. 1, high-pressure washing very efficiently reduces the amount of hydrocyanic acid contained in the compressed gas stream 76, down to a content of between 50 ppmV and 500 ppmV for example. This efficiency is made possible by means of one-through water circulation. However, a substantial water flow is required to maximise wash efficiency and use of the aqueous phase 70, which essentially corresponds to the water of the gas stream 12 condensed in the quench/wash unit 30, limits and even eliminates the need to replenish with additional fresh water (boiler feed water). In installation 10 in FIG. 1, the wash water 50 is boiler feed water which has to be conveyed as far as the unit and therefore represents an operating cost, whilst in installation 110 in FIG. 2 the wash water corresponds to the aqueous phase 70 produced inside the unit.

In the installation 10 in FIG. 1, the flow of water 54 to be routed to the external water treatment unit corresponds to the combined flow of the aqueous phase 70 and of the water collected at outlet 53, whilst in installation 110 in FIG. 2 it is strongly reduced and only corresponds to the flow of water collected at outlet 53. This arrangement reduces operating costs of the installation 10 and of the downstream water treatment installation.

The invention claimed is:

1. A process for treating at least one gas stream derived from pyrolysis of plastic and/or biomass, the process comprising:

quenching and washing with water the gas stream derived from pyrolysis of plastic and/or biomass in a quench/wash unit, and separating an aqueous phase from a washed gas stream;

compressing then cooling the washed gas stream to form a compressed gas stream;

washing the compressed gas stream under pressure to form a second washed gas stream;

passing the second washed gas stream through at least one acid removal unit to form an acid-depleted gas stream whereby carbon dioxide is removed from the second washed gas stream;

drying the acid-depleted gas stream to form a dry gas stream;

passing the dry gas stream through at least one impurity removal unit to form a purified gas stream; and feeding the purified gas stream into a cryogenic absorption unit and supplying the cryogenic absorption unit with a hydrocarbon cryogenic solvent to obtain a light gas residue at a first outlet of the cryogenic absorption unit, and a fraction of C2+ hydrocarbons at a second outlet of the cryogenic absorption unit.

2. The process according to claim 1, wherein the gas stream derived from pyrolysis contains C2+ hydrocarbons and light carbons, including hydrogen and methane.

3. The process according to claim 1, wherein the gas stream derived from pyrolysis contains one or more of:

carbon containing components including carbon monoxide, carbon dioxide, nitrogen oxides and/or oxygen and oxygen derivatives including alcohols, aldehydes and/or ketones; and/or nitrogen-containing compounds, including nitrogen and ammonia; and/or acid compounds including hydrochloric acid and hydrocyanic acid; and/or, chlorine-containing compounds; and/or sulfur-containing compounds including mercaptans, carbon oxysulfides and hydrogen sulfide.

4. The process according to claim 1, wherein the hydrocarbon cryogenic solvent comprises C3 hydrocarbons and/or C4+ hydrocarbons.

5. The process according to claim 1, comprising separating the fraction of C2+ hydrocarbons into a fraction of C2 hydrocarbons and into at least one fraction of C3+ hydrocarbons, at least part of said fraction of C3+ hydrocarbons being recycled in the cryogenic absorption unit.

6. The process according to claim 5, wherein the separating comprises the production of a fraction of C3 hydrocarbons and a fraction of C4+ hydrocarbons, at least part of the fraction of C3 hydrocarbons being recycled in the cryogenic absorption unit.

7. The process according to claim 1, wherein the light gas residue contains fuel gas, including methane, hydrogen, and light compounds of the purified gas stream, the light compounds including carbon monoxide, nitrogen, nitrogen monoxide and/or oxygen.

8. The process according to claim 1, further comprising, conveying the light gas residue into a cracking unit including the combustible gas network of a steam cracker and/or is intended to form a fuel gas.

9. The process according to claim 1, wherein at least one acid removal unit comprises an amine unit or/and a caustic wash unit, the compressed gas stream passing through the amine unit or/and the caustic wash unit.

10. The process according to claim 1, wherein the impurity removal unit comprises at least one activated metal bed, including an activated alumina bed or a mixed adsorbent configured to retain one or more compounds from the dry gas stream on the at least one activated metal bed of the one or more compounds being selected from a list comprising:

sulfur-containing compounds including hydrogen oxysulfide and mercaptans, and/or ammonia, and/or nitrogen-containing compounds, and/or chlorine-containing compounds, and/or oxygen-containing compounds including alcohols, and/or silicones contained in the dry gas stream.

11. The process according to claim 1, wherein at least one part of the fraction of C2+ hydrocarbons is fed into a cracker able to produce an ethylene fraction or into a self-contained unit able to produce an ethylene fraction.

12. The process according to claim 1, wherein at least one part of the aqueous phase produced at the quenching/washing is pressurized and placed in contact with the compressed gas stream at the high-pressure washing.

13. The process according to claim 1, further comprising, placing at least two streams from among the purified gas stream, the hydrocarbon cryogenic solvent, the light gas residue, and/or at least one reflux or condensate of the cryogenic absorption unit in heat exchange contact with one another in a cold box formed of a single item of plate-fin cryogenic equipment, comprising brazed aluminum.

14. A process for treating at least one gas stream derived from pyrolysis of plastic and/or biomass, the process comprising:

quenching and washing with water the gas stream derived from pyrolysis of plastic and/or biomass in a first quench/wash unit, and separating an aqueous phase from a washed gas stream;

compressing then cooling the washed gas stream to form a compressed gas stream;

providing the compressed gas stream and a washing fluid to a second wash unit and washing the compressed gas stream under pressure in the second wash unit having a high-pressure washing chamber to form a second washed gas stream;

passing the second washed gas stream through at least one acid removal unit to form an acid-depleted gas stream drying the acid-depleted gas stream to form a dry gas stream;

passing the dry gas stream through at least one impurity removal unit to form a purified gas stream; and feeding the purified gas stream into a cryogenic absorption unit and supplying the cryogenic absorption unit with a hydrocarbon cryogenic solvent to obtain a light gas residue at a first outlet of the cryogenic absorption unit, and a fraction of C2+ hydrocarbons at a second outlet of the cryogenic absorption unit.

15. The process according to claim 14, further comprising, placing at least two streams from among the purified gas stream, the hydrocarbon cryogenic solvent, the light gas residue, and at least one reflux or condensate of the cryogenic absorption unit in heat exchange contact with one another in a cold box formed of a single item of plate-fin cryogenic equipment in brazed aluminium.

16. A process for treating at least one gas stream derived from pyrolysis of plastic and/or biomass, the process comprising:

quenching and washing with water the gas stream derived from pyrolysis of plastic and/or biomass in a first quench/wash unit, and separating an aqueous phase from a washed gas stream;

compressing then cooling the washed gas stream to form a compressed gas stream;

providing the compressed gas stream and a washing fluid to a second wash unit and washing the compressed gas stream under pressure in the second wash unit having a high-pressure washing chamber to form a second washed gas stream;

passing the second washed gas stream through at least one acid removal unit to form an acid-depleted gas stream;

drying the acid-depleted gas stream to form a dry gas stream;

passing the dry gas stream through at least one impurity removal unit to form a purified gas stream;

feeding the purified gas stream into a cryogenic absorption unit and supplying the cryogenic absorption unit with a hydrocarbon cryogenic solvent to obtain a light gas residue at a first outlet of the cryogenic absorption unit, and a fraction of C2+ hydrocarbons at a second outlet of the cryogenic absorption unit;

feeding the fraction of C2+ hydrocarbons to a fractionating column and separating the fraction of C2+ hydrocarbons into a fraction of C2 hydrocarbons, a fraction of C3+ hydrocarbons, a fraction of C3 hydrocarbons, and a fraction of C4 hydrocarbons; and recycling at least a portion of the fraction of C3+ hydrocarbons to an inlet side of the cryogenic absorption to mix with the cryogenic solvent; and feeding a remaining fraction of the C2 hydrocarbons, a fraction of C3+ hydrocarbons, a fraction of C3 hydrocarbons, and a fraction of C4 hydrocarbons, and the light residue to a cracking installation.

17. The process according to claim 16, wherein the washing fluid is pressurized water.

18. The process according to claim 16, wherein the washing fluid is the aqueous phase separated from washed gas stream in the first quench/wash unit, and further comprising, providing the aqueous phase from the first quench/wash unit to an inlet of the high-pressure wash chamber of the second wash unit.

19. The process according to claim 16, wherein the washing fluid is pressurized water.

* * * * *